United States Patent [19]

Fujihira et al.

[11] Patent Number: 5,304,795
[45] Date of Patent: Apr. 19, 1994

[54] HIGH RESOLUTION OBSERVATION APPARATUS WITH PHOTON SCANNING MICROSCOPE

[75] Inventors: Masamichi Fujihira, Yokohama; Tatsuaki Ataka; Toshihiro Sakuhara, both of Tokyo, all of Japan

[73] Assignees: Seiko Instruments Inc.; Masamichi Fujihira, both of Japan

[21] Appl. No.: 954,317

[22] Filed: Sep. 30, 1992

[30] Foreign Application Priority Data

Oct. 3, 1991 [JP] Japan .................. 3-256817

[51] Int. Cl.$^5$ .............................. H01J 3/14
[52] U.S. Cl. ................. 250/234; 250/227.11; 250/306
[58] Field of Search ............ 250/216, 234, 227.11, 250/306, 307; 356/376

[56] References Cited

U.S. PATENT DOCUMENTS 5,018,865 5/1991 Ferrell et al. ............... 250/227.11

FOREIGN PATENT DOCUMENTS 0308537 3/1989 European Pat. Off. .
0426571 5/1991 European Pat. Off. .
0469879 2/1992 European Pat. Off. .
9004753 5/1990 PCT Int'l Appl. .

OTHER PUBLICATIONS

Durig, et al., "Near-field Optical Scanning Microscopy with Tunnel-Distance Regulation", IBM Journal of Research and Development, vol. 30, No. 5, Sep. 1986, NY, pp. 478-480.

Betzig, et al., "Combined Shear Force and Near-field Scanning Optical Microscopy", Applied Physics Letters, vol. 60, No. 20, May 18, 1992, NY, pp. 2484-2486.

Toledo-Crow, et al., "Near-field Differential Scanning Optical Microscope With Atomic Force Regulation", Applied Physics Letters, vol. 60, No. 24, Jun. 15, 1992, NY, pp. 2957-2959.

Primary Examiner—David C. Nelms
Attorney, Agent, or Firm—Bruce L. Adams; Van C. Wilks

[57] ABSTRACT

A high resolution observation apparatus of material features with a photon scanning microscope. The apparatus detects evanescent light which depends on surface feature of a sample and detects detailed distribution of optical constants of the sample. Namely, the apparatus makes it possible to detect detailed distribution of transparency or refractive index within a sample material in higher resolution than the wavelength of the incident light which is irradiates to the sample material coated on the top surface of the optical prism. The apparatus includes means for maintaining a predetermined distance between the sample and an optical fiber tip or means for detecting a positioning signal. Further, it becomes possible to detect fluorescent condition of the sample.

17 Claims, 4 Drawing Sheets

HIGH RESOLUTION OBSERVATION APPARATUS WITH PHOTON SCANNING MICROSCOPE

BACKGROUND OF THE INVENTION

This invention relates to a high resolution observation apparatus with a photon scanning microscope for detecting evanescent light which depends on material features of a sample by irradiating light to the sample at a total reflection angle.

As shown in FIG. 2, a photon scanning microscope conventionally, for example as described in "Kougaku" Vol. 20, No. 3 p.p. 134-141, generates the light which is emitted from a semiconductor laser optical source 8 and which has a single wavelength to be incident to a prism 1 at a total reflection angle, and detects evanescent light which is emitted depending on the topography of a surface of a sample 2 on the prism 1 by an optical fiber probe 3 with a minute opening and an optical detecting system 10.

Then, the optical fiber probe 3 scans the sample in x and y-axis directions while controlling the z-axis direction so that the detected evanescent light should be constant, and the control signal and the scanning signals are processed, and thereby a three-dimentional shape of the sample surface is determined. Moreover, only light having the same wavelength as of the incident light that is detected.

However, the photon scanning microscope is conventionally used for observing the topography of the sample surface and the observation is performed with the precondition that the sample is scanned so that the detected evanescent light is constant and that the evanescent light depends on the distance between the sample surface and the probe tip.

Therefore, if the sample includes materials with different transparency or different refractive index from the rest of the sample, incorrect topography is observed. Moreover, it is essentially impossible to detect the difference in transparency or the difference in refractive index within the sample.

For example, in FIG. 3A, the sample 22 has a wave shape surface 22a and has an uniform optical constant, such as transparency or refraction index. In this case, when light 21 is incident to a prism 1 at a total reflection angle and an evanescent light emitted from the sample 2 by the incident light 21 is detected by an optical fiber tip 3, a locus 23 of the optical fiber tip results in a flat shape after scanning the optical fiber tip above the sample surface with controlling the z-axis direction so that the detected evanescent light is constant. The conventional photon scanning microscope, therefore, can not observe the sample surface 22a correctly if the sample has a uniform optical constant.

In another example shown in FIG. 3B, the sample 24 has a flat surface and has singular regions 24a which have a different optical constant, such as transparency or refraction index, from the remaining regions 24b of the sample 24. In this case, when light 21 is incident to a prism 1 at a total reflection angle as the same manner in the above example, a locus 25 of the optical fiber tip results in a wave shape after scanning the optical fiber tip because the singularity of the optical constant within the sample affects the evanescent light emitted by the incident light. The conventional photon scanning microscope can not observe the sample surface correctly, either, if the sample has some singular region of optical constants even if it has a flat surface.

Further, only the evanescent light emitted by the wavelength of the incident light is detected because the detected light has the same wavelength as that of the incident light. It is, therefore, impossible to observe fluorescent condition of the sample in other wavelength than that of the incident light.

Moreover, in a general optical observer, the resolution of observation is limited by optical diffraction limit. Namely, the resolution is at the same level as that of the wavelength of the incident light.

SUMMARY OF THE INVENTION

It is an object of the present invention to provide an apparatus for detecting the detailed distribution of transparency or refractive index within the sample material.

It is another object of the present invention to provide an apparatus for detecting a fluorescent condition of the sample material by detecting light which has a different wavelength from that of the incident light.

It is a further object of the present invention to provide an apparatus for detecting many kinds of optical information from the sample by using an incident light including at least two wavelengths.

It is an even further object of the present invention to provide an apparatus for observing optical information in the sample at a resolution less than the wavelength of the incident light used by the apparatus.

In order to achieve the above mentioned objects, the intensity of evanescent light emitted from the sample is detect by fixing the position of the optical fiber tip on z-axis above the sample surface in a constant distance or by controlling the distance between the optical fiber tip and the sample surface in z-axis so as to keep the detected intensity signal constant.

Further, the intensity of the evanescent light which is emitted by one of those wavelengths of the incident light is used as the signal for controlling the position of the optical fiber tip on the z-axis, and the intensity of the evanescent light which is emitted in another wavelength is detected for observing the fluorescent condition of the sample material.

In order to observe the distribution of transparency or refractive index within the sample material, the inventive apparatus includes has an optical detecting system for detecting the signal for maintaining the predetermined distance between the sample surface and the optical fiber tip a, z-axis moving unit for maintaining the detected signal constant, and an x and y-axis moving unit for scanning the sample surface by the fiber tip to detect the intensity of the evanescent light from the sample material by the incident light.

As to a mechanism for maintaining the predetermined distance between the sample and the optical fiber tip, there is a unit for keeping the x-y plane corresponding to the sample surface which is scanned by the fiber tip and the prism top surface which is coated with the sample parallel with each other. This unit enables the fiber tip to scan the sample surface as the fiber tip keeps the predetermined distance from the sample surface when it scans the sample of uniform thickness.

In case a part of the fiber which is adjacent to an opening of the fiber tip and a sample material are both made of the material having electrical conductivity, a scanning tunnel microscope mechanism can be used for keeping the tunnel current which flows between the conductive part of the fiber and the sample constant. Then, tunnel current between the sample surface and the fiber tip is detected, and the z-axis moving unit is adjusted by the z-axis control unit so that the tunnel current is constant.

Another mechanism for controlling the distance between the sample and the optical fiber tip is an atomic force microscope. This mechanism has a cantilever for detecting the interatomic force between the sample surface and the cantilever. The cantilever is disposed at a part of the fiber which is adjacent to an opening of the fiber tip. In this case, the conductivity of the sample does not matter. By this mechanism, the distance between the sample surface and the fiber tip is controlled so that the interatomic force between them is constant.

Additionally, as the signal for maintaining the predetermined distance between the sample and the optical fiber tip, any signals which are detected on the principles of detecting with the scanning X microscope (SXM), or a new type of microscope which derives from the principle of the scanning tunnel microscope, are available. These signals include signals which correspond to magnetic force, frictional force, ultrasonic wave, heat, ionic conductivity and other physical parameters. When these signals are detected, the distance between the sample surface and the fiber tip is kept at the predetermined distance by using the z-axis control unit and the z-axis moving unit so that the detected signal is constant. In this condition, light is generated to be incident to the top surface of the prism which is coated with the sample at a total reflection angle, and the optical fiber tip scans to detect the evanescent light in the x-y plane of the sample surface. At this time, the evanescent light is emitted from the top surface of the prism if the refractive index of the sample is lower than that of the prism, and is emitted from the sample surface on the prism if the refractive index of the sample is higher than that of the prism. In both cases, the intensity of the evanescent light changes depending on the transparency or the refractive index of the sample.

It is possible to detect the distribution of the transparency or the refractive index of a minute region within the sample material by scanning the sample surface in the x and y-axis directions while detecting the intensity of the evanescent light. The x and y-axis moving unit and the z-axis moving unit can be provided at either the optical fiber side or the sample side. The opening of the optical fiber tip for detecting the evanescent light has an opening size smaller than the wavelength of the light to be detected.

Furthermore, when the sample emits fluorescent light with a different wavelength from that of the incident light, the fluorescent light can also be detected by providing the optical detecting unit as having means for detecting at least two wavelengths of light. Moreover, by generating the incident light having at least two wavelengths, the evanescent light which is emitted by one of the wavelengths of the incident light is used as means for maintaining the predetermined distance between the sample and the optical fiber tip, and another evanescent light by another wavelength of the incident light is used for observing optical constants of the sample material.

In a high resolution observation apparatus with a photon scanning microscope with such a structure as mentioned above, each of the optical constants such as transparency and refraction index can be measured as clearly separated information, though in conventional devices, the optical constants are measured as one combined information with the distance between the sample and the optical fiber tip. In other words, in contrast with the present invention, the information of the distance and the optical constants can not be separated by the conventional apparatus.

In the present invention, the signal for maintaining the predetermined distance between the sample and the optical fiber tip is detected, and the optical fiber tip is positioned on the z-axis to the sample so that the detected signal is constant. Therefore, the intensity of the evanescent light can be detected, and the distribution of the transparency or the refractive index within the x-y plane of the sample can be measured at a resolution smaller than the wavelength of the incident light.

For example, in FIG. 4, the sample 26 has a wave shape surface 26c and has singular regions 26a which has a different optical constant, such as transparency or refraction index, from the rest 26b of the sample 26. In this case, when light 28 having at least two wavelengths is incident to a prism 1 at a total reflection angle and an evanescent light emitted from the sample 2 by the incident light 28 is detected by an optical fiber tip 3, a locus 27 of the optical fiber tip results in a wave shape, which traces the shape of the sample surface 26c, after scanning the optical fiber tip above the sample surface 26c while controlling the z-axis direction so that the detected evanescent light with one of the wavelengths is constant. The optical constants can also be measured by detecting the evanescent light with the other wavelength. The apparatus of the present invention, therefore, can observe both the sample surface 26c correctly and detailed distribution of optical constants within the sample.

This apparatus can be used not only as an observation apparatus for observing detailed transparency or refractive index of the sample material but also as an optical reader for retrieving information written as different transparency or refractive index having a resolution smaller than the wavelength for some photochromic materials. Namely, the apparatus can be utilized as ultra-high density optical read/write memory system.

Further, fluorescent condition of the sample material can be observed by detecting at least two wavelength of emitted light.

When incident light having at least two wavelengths is used, the evanescent light which is emitted by one of the wavelengths of the incident light can be used as means for maintaining the predetermined distance between the sample and the optical fiber tip as described before. As the wavelength for that means, it is important to select such a wavelength as not to affect largely the transparency and the refractive index of the sample material. As the evanescent light which is emitted by the wavelength is not influenced so much by the transparency or refractive index of the sample, the intensity of the evanescent light clearly depends on the distance between the sample and the optical fiber tip in the z-axis direction. It is possible to measure the optical constants by controlling the z-axis as the evanescent light of one wavelength is constant and by detecting the intensity of the light which is emitted by another wavelength of the incident light.

As described above, every optical constant, such as transparency and refraction index, can be measured by optical methods including the control of the position of the optical fiber tip in a predetermined distance above the sample surface in the z-axis.

DETAILED DESCRIPTION OF THE PREFERRED EMBODIMENTS

Embodiments of the present invention will be explained in reference to the drawings.

Figure 1A:
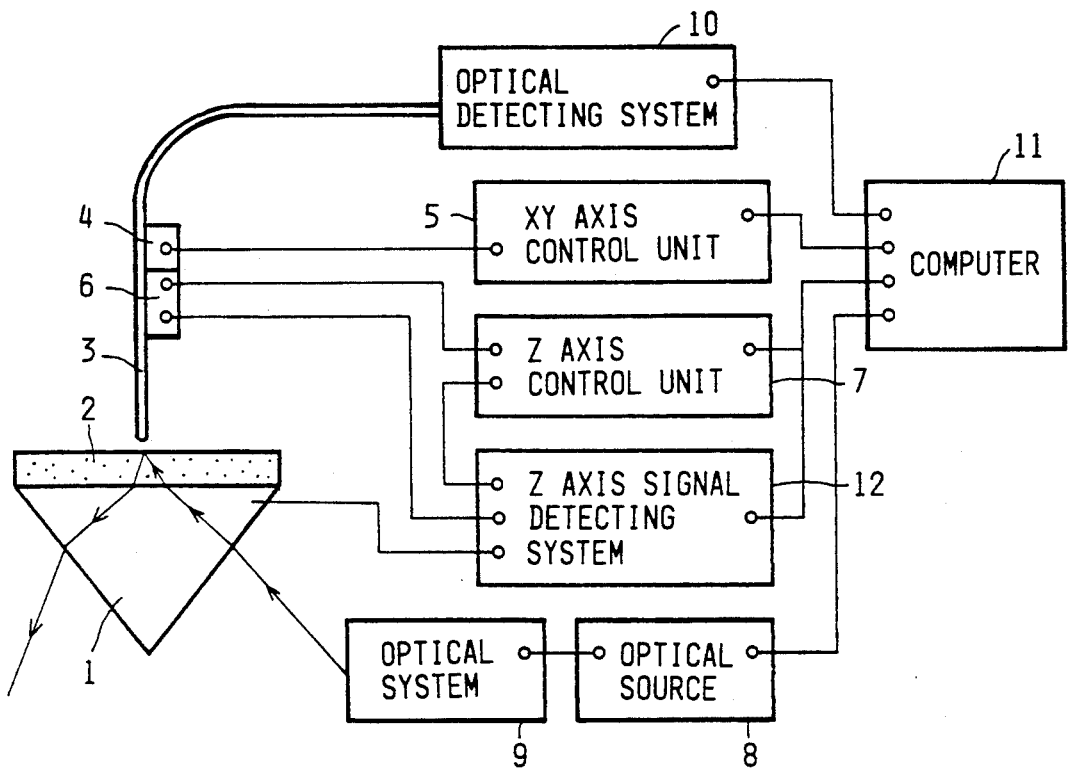
FIG. 1A is a sectional view showing an embodiment of the high resolution observation apparatus with a photon scanning microscope in accordance with the present invention.

FIG. 1A is a schematic view showing the high resolution observation apparatus with a photon scanning microscope of the present invention. A sample 2 is coated on a top surface of a prism 1, and light having a specific wavelength is generated by an optical source 8 and an optical system 9 so as to be incident to the sample 2 or the top surface of the prism 1 at a total reflection angle. As the optical source 8, mercury, xenon or halogen lamps, and helium-neon, argon ion or semiconductor lasers can be used. At this time, the intensity of the evanescent light which is emitted from the surface of the sample 2 is detected by an optical fiber 3 and an optical detecting system 10.

Figure 1B:
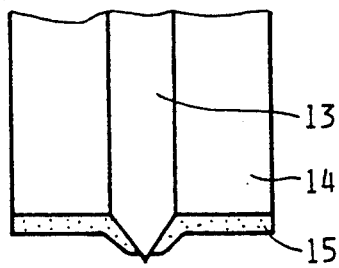
FIG. 1B is a sectional view of showing an outline of the optical fiber tip.
Figure 2:
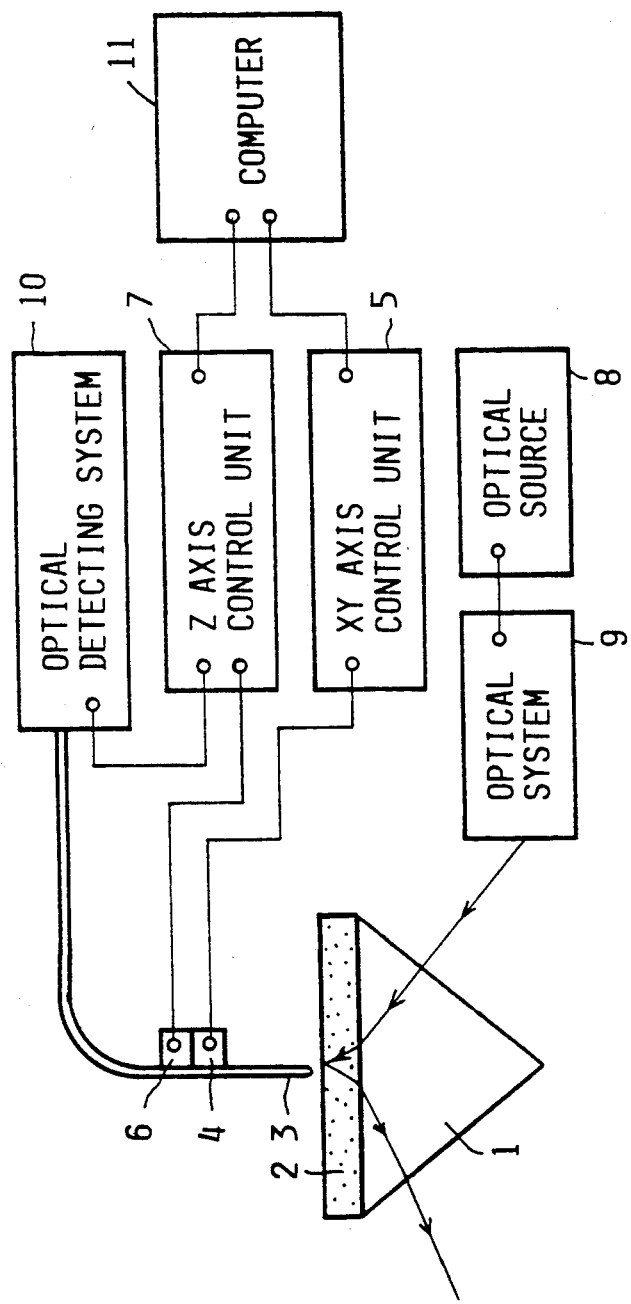
FIG. 2 is a sectional view of the conventional photon scanning microscope.
Figure 3A:
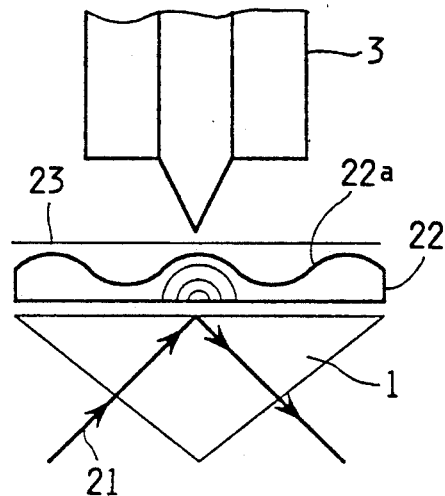
FIG. 3A is an explanatory view of a measuring example of the conventional photon scanning microscope.
Figure 3B:
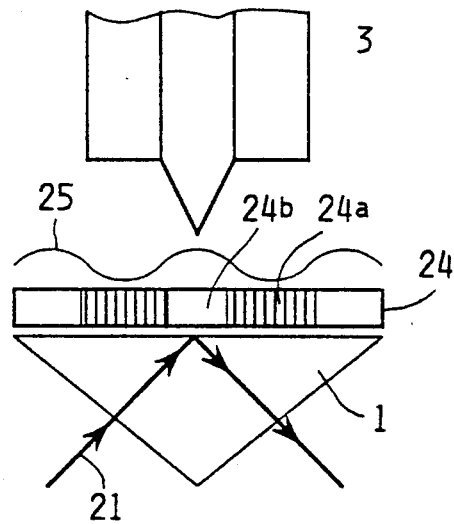
FIG. 3B is an explanatory view of another measuring example of the conventional photon scanning microscope.
Figure 4:
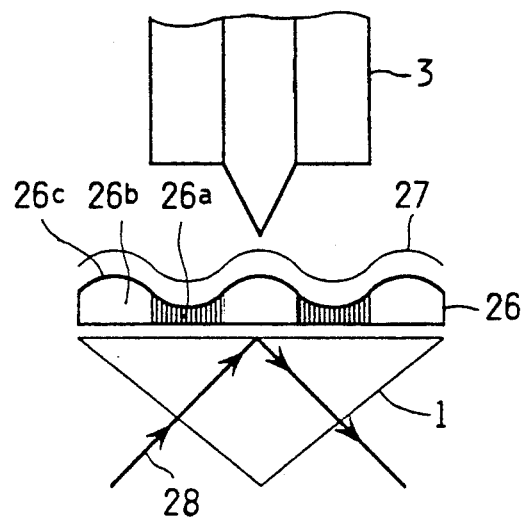
FIG. 4 is an explanatory view of a measuring example of high resolution observation apparatus with a of photon scanning microscope in accordance with the present invention.

The optical fiber tip needs to be provided with a minute opening in order to detect, the evanescent light. This minute opening is smaller in size than the wavelength of the incident light. FIG. 1B shows a magnified drawing of the fiber tip.

In order to fabricate the fiber tip, first of all, the end face of the optical fiber is cut so as to be vertical to the optical fiber axis. The cut surface is abraded to produce an exact horizontal plane if necessary. The optical fiber tip is etched with a mixed liquid of fluorine and ammonium fluoride in the ratio of one to five for ninety minutes, thereby an optical fiber clad portion 14 is removed from the optical fiber tip and the tip of an optical fiber core portion 13 is sharpened. In order to realize an opening which is smaller than the wavelength in size, the tip is deposited with chrome and gold as a light shielding film 15, and the very tip portion is removed by means of plasma etching, electrolyte etching and so on. A fabricating process of the fiber tip is not limited to the above method but may be fabricated using any of the methods available.

To maintain the predetermined distance between the optical fiber tip and the sample surface, a z-axis signal detecting system 12 detects the signal for maintaining the predetermined distance between the optical fiber tip and the sample surface, and a z-axis control unit 7 controls a z-axis moving unit 6 so that the detected signal is constant. The signals used for this process include several kinds of physical parameter as described below.

In one way, a mechanism of the scanning tunnel microscope (STM) can be used for detecting tunnel current flowing between a part of the fiber and the sample if both of the part of the fiber which is adjacent to the opening of the fiber tip and the sample material have electrical conductivity. The tunnel current is the signal for maintaining the z-axis distance.

In another way, a mechanism of the atomic microscope (AFM) can be used for detecting interatomic force between a cantilever provided at a part of the fiber which is adjacent to the opening of the fiber tip and the sample surface. The interatomic force is the signal for maintaining the z-axis distance. In this case, it does not matter whether the sample material is electrically conductive or not.

Additionally, as a detecting signal for this purpose, any signals which are detected on the principle of detecting with the scanning X microscope (SXM), or a new type of microscope that derives from the principle of the scanning tunnel microscope, are available. They include signals which correspond to magnetic force, frictional force, ultrasonic wave, heat and ionic conduction respectively.

Another embodiment of the z-axis signal detecting system 12 is so structured that the fiber tip is fixed in constant distance above the sample surface on the z-axis. One of the mechanisms for fixing the distance constant is the unit for making the x-y plane which is scanned by the fiber tip and the top surface of the prism which is coated with the sample to be parallel with each other. If the film thickness of the sample is uniform, the fiber tip can scan the sample surface in the fixed distance above the sample surface by use of this unit.

While the z-axis is controlled by any of the above ways, an x and y-axis moving unit 4 is controlled by an x and y-axis control unit 5 and the x-y plane is scanned. The x and y-axis moving unit 4 and the z-axis moving unit 6 may be provided either on the optical fiber 3 side or the prism 1 side. Any of the x and y-axis control unit 5, the z-axis signal detecting system 12, the z-axis control unit 7, the optical source 8, and the optical detecting system 10 can be controlled by a computer 11.

MEASUREMENT EXAMPLE 1

In this example, the apparatus shown in FIG. 1 is used, and as the mechanism for positioning on the z-axis, there is used a unit for making the x-y plane which is scanned by the fiber tip and the top surface of the prism which is coated with the sample parallel with each other. As the sample, this example uses striped patterns having gaps of 1 (one) micrometer in width on the prism by using a 1 (one) micrometer wide gold pattern. The film thickness of the gold is 10 nanometer. An incident light is irradiated on the prism by a semiconductor laser having a 780 nanometer wavelength so as to be incident to the prism at a total reflection angle in the condition that the x-y plane of the apparatus and the top surface of the prism are made to be parallel with each other. The sample and the optical fiber tip are brought close to each other enough to detect the evanescent light, and the z-axis position of the optical fiber tip is fixed at this position and then the x-y plane is scanned. Measuring the intensity of the evanescent light determines the striped pattern which indicates different intensities in every width of 1 (one) micrometer which corresponds to the gold pattern coated on the prism surface.

MEASUREMENT EXAMPLE 2

In this example, the mechanism for positioning on the z-axis is the same as that of the example 1. For preparing the sample, methylene blue is dissolved into polyvinyl solution, the solution is cast on the prism and then the moisture of the solution is evaporated, and the residue is used as the sample. An incident light is irradiated on the prism by a helium-neon laser having a 633 nanometer wavelength so as to be incident to the prism at a total reflection angle in the condition that the x-y plane which is scanned by the fiber tip and the top surface of the prism which is coated with the sample are made parallel with each other. The sample and the optical fiber tip are brought close to each other enough to detect the evanescent light, and the z-axis is fixed at that position, and then the x-y plane is scanned. The result of measuring the intensity of the evanescent light shows a density distribution of the sample which corresponds to the optical absorption of the methylene blue because the methylene blue has an absorption band around the wavelength of 630 nanometer.

MEASUREMENT EXAMPLE 3

In this example, the positioning of the optical fiber tip and the sample surface on the z-axis is done by detecting the positioning signal with the z-axis signal detecting unit. The z-axis control unit controls the z-axis moving unit so that the detected signal is constant. As to the positioning signal, the tunnel current flowing between the optical fiber and the sample is used with a mechanism of the scanning tunneling microscope in the condition that both a part of the fiber which is adjacent to the opening of the fiber tip and the sample material have electrical conductivity. As the sample, a polypyrrole thin film is coated on the prism surface. While the tunnel current flowing between the polypyrrole thin film and the conductive part of the optical fiber is kept constant, an incident light having a 488 nanometer wavelength is irradiated on the prism by an argon ion laser, and the intensity of the evanescent light which has the same wavelength as that of the incident light is measured. The measurement determines intensity distribution of the evanescent light within the polypyrrole film. The intensity distribution corresponds to the distribution of the doping amount of an ion within the film, the amount of which is changed by an electrolytic process for the sample in advance.

Moreover, this measurement can also be done with the system that the sample and the optical fiber tip are dipped into an electrolytic solution. In this system, a saturated calomel electrode is used as a reference electrode and platinum is used as a counter electrode, and both are set in the above electrolytic solution. The sample and the optical fiber tip are used as working electrodes respectively, the electrical potential of the two electrodes is controlled. The position of the z-axis is controlled so that the tunnel current flowing between the two electrodes is kept constant. Then, an incident light having a 488 nanometer wavelength is irradiated so as to be incident to the prism by an argon ion laser, and the intensity of the evanescent light having the same wavelength as that of the incident light is measured. Thereby, the intensity distribution of the evanescent light is determined within the sample in the electrolytic solution as well as in the atmosphere. The result of measurement of the intensity distribution corresponds to the distribution of the doping amount of ion within the sample film.

MEASUREMENT EXAMPLE 4

In this example, the positioning is done by the same as that of the example 3. As to the positioning signal, interatomic force between the sample and the cantilever tip is used with a mechanism of the atomic force microscope. In the mechanism, a cantilever for detecting interatomic force is provided at a part of the fiber which is adjacent to the opening of the fiber tip.

Figure 5:
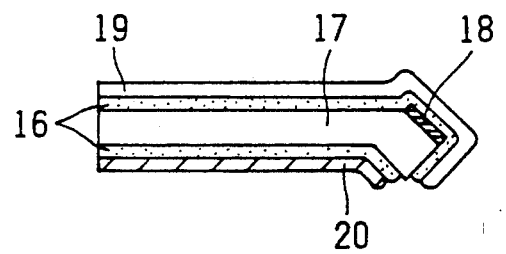
FIG. 5 is a sectional view showing an outline of the optical fiber for detecting the interatomic force in accordance with the present invention.

FIG. 5 is a schematic view of one embodiment of the cantilever equipped with an optical wave guide. In this case, the optical wave guide is used as a probe for detecting the evanescent light instead of the general optical fiber, which can also be regarded as one type of optical fiber.

In the fabrication process of the optical wave guide, a pyramidal hole is made on a part of the silicon substrate 20 by anisotropic etching. The surface of the substrate 20 is made into silicon oxide 16 by way of thermal oxidation, afterwards a glass 17 that is an optical wave guide is formed by a vacuum process. A part of the glass 17 is etched, and then a reflective mirror 18, the silicon oxide 16, and a chrome oxide 19 are formed on the glass 17 also in a vacuum process. Then, an unnecessary part of the silicon substrate 20 is removed by etching with a thin layer of the silicon to be left so as to form the shape of a cantilever. The very tip portion of the pyramidal tip is made into an opening by removing the silicon and the silicon oxide from the very tip portion so that the opening is smaller than the wavelength of the incident light in size.

The cantilever including the optical wave guide of the above structure functions enough as a cantilever for detecting the interatomic force, and the optical wave guide is also able to detect the evanescent light.

As the sample, poly-vinyl cinnamate, an example of a photoresist material, is coated and exposed in some pattern on the prism surface. While the position of the cantilever above the sample surface in the z-axis direction is controlled so that the interatomic force is kept constant, the intensity of the evanescent light is measured by scanning the sample surface in the x and y-axis directions, which determines the intensity distribution of the evanescent light corresponding to the pattern which is exposed in the prior step.

MEASUREMENT EXAMPLE 5

In this example, the optical detecting system 10 in FIG. 1 detects a plurality of wavelengths of light (not only the same wavelength as that of incident light but also different wavelengths of light) caused by the incident light or a fluorescent effect of the sample.

The same mechanism as that of examples 1 and 2 is used for positioning on the z-axis by making the x-y plane which is scanned by the fiber tip and the top surface of the prism which is coated with the sample to be parallel with each other. As to the sample, stilbene, which is an example of a fluorescent material, is coated on the prism surface. An incident light is irradiated on the prism by ultraviolet light generated by a xenon lamp. The stilbene fluorescent material absorbs ultraviolet light and emits fluorescence having a 430 nanometer wavelength. Therefore, the optical detecting system 10 is formed to detect light having a wavelength around 430 nanometer in length distinctively by incorporating an optical filter into the optical detecting system 10.

The result of the measurement determines intensity distribution of the light having a 430 nanometer wavelength which is different from that of the incident light, and the measured light is verified to be fluorescence from the sample.

Further, it becomes possible to detect light having multi-wavelengths by incorporating a grating and a photodiode array into the optical detecting system 10. Therefore, as a result of the similar measurement, the evanescent light, which have the same wavelength as that of the incident light and the fluorescence caused by the incident light can be detected simultaneously.

MEASUREMENT EXAMPLE 6

In this measurement example, the optical source 8 in FIG. 1 generates light having two wavelengths by using two lasers, by using the SHG effect, or by using a lamp. In this case, the optical detecting system 10 detects a plurality of wavelengths of light as in Example 5.

The optical detecting system 10 detects the evanescent light excited by one of the wavelengths of the incident light, and sends the result to the z-axis signal detecting system 12 and the z-axis control unit 7 through the computer 11 in order to use it as the signal for positioning on the z-axis. Then, the computer 11 controls the z-axis moving unit 6, and positions the optical fiber tip on the z-axis so that the intensity of the detected evanescent light is constant. For this positioning, it is necessary to use the incident light having such wavelength as not to cause a optical absorption of the sample material.

In this example, Prussian blue is used as the sample, and light having two wavelengths, 680 nanometer wavelength and 800 nanometer wavelength, is used as the incident light. The evanescent light which is emitted by the incident light having 800 nanometer wavelength is used as the signal for positioning on the z-axis. Prussian blue has an absorption band around the wavelength of 680 nanometer, but does not have it around the wavelength of 800 nanometer. Therefore, the evanescent light excited by the incident light having this wavelength of 800 nanometer is not influenced by the optical absorption of the sample. The intensity of the evanescent light depends on the distance, so that the evanescent light is suitable to be used as the signal for positioning on the z-axis. The measuring result of the intensity of the evanescent light excited by the incident light having 680 nanometer wavelength determines the distribution of optical absorption which corresponds to the distribution of the Prussian blue.

MEASUREMENT EXAMPLE 7

In this example, the same apparatus as that of example 6 is used. As to the sample, spiropyrane compound, which is one of the photochromic material, is coated and exposed in some pattern by ultraviolet rays in advance. An incident light having 800 nanometer wavelength and 540 nanometer wavelength is irradiated to the prism so as to reflect at a total reflection angle.

The 800 nanometer wavelength light penetrates both the colored portion and the transparent portion, and does not cause photochromic reaction. The 540 nanometer wavelength light does not cause photochromic reaction, but is absorbed in the colored portion. The sample is scanned in the x and y-axis directions by controlling the position on z-axis so that the intensity of the evanescent light excited by the incident light having the 800 nanometer wavelength should be kept constant. As a result of measuring, the intensity distribution of the evanescent light, which is excited by the 540 nanometer wavelength incident light, corresponds to the pattern which is formed on the prism surface by ultraviolet rays in advance.

ADVANTAGE OF THE INVENTION

As explained above, the present invention has such a substrate such that there is detected the signal for maintaining the predetermined distance on the z-axis between the sample and the optical fiber tip, there is provided means for keeping the detected signal constant, and thereby the intensity of the evanescent light is detected. Accordingly, it results in the effect that it is possible to measure the distribution of transparency and refraction index within the x-y plane of the sample with resolution less than the wavelength in size.

Further, the present invention has a structure such that light having a different wavelength from that of the incident light can also be detected, and light including a plurality of wavelengths can also be detected. Such a structure enables detection of not only the evanescent light having the same wavelength as that of the incident light, but also detection of light having another wavelength. Therefore, fluorescent condition of the sample material can also be detected.

Moreover, the present invention has a structure such that the intensity of the evanescent light generated by one of the wavelengths of the incident light is used as the signal for controlling the position on the z-axis, thereby the intensity of the evanescent light generated by another wavelength is detected for observing optical parameters, such as transparency or refraction index, of the sample material.

The present invention also enables both the observation of optical constants of the sample, and the control of the position of optical fiber tip by an optical method only.

What is the claimed is:

1. A high resolution observation apparatus with a photon scanning microscope comprising:
   an optical device having a surface on which a sample to be observed is coated;
   an optical source for generating an incident light of a predetermined wavelength to be incident to the sample through the optical device at a total reflection angle which is defined by refraction indices of the optical device and the sample;
   an optical detecting probe having an opening at a tip of the probe for receiving a sample light emitted from the sample surface in response to the incident light;
   an optical detecting system for detecting the sample light received by the optical detecting probe having different wavelengths than the predetermined wavelength of the incident light;
   an x and y-axis control unit for moving the optical detecting probe to scan the sample surface over a two-dimentional area to be observed; and
   a z-axis control unit for positioning the optical detecting probe at a distance above the sample surface close enough to detect the sample light and for controlling a position of the optical detecting probe so as to keep a positioning signal detected by the optical detecting system constant during a course of scanning the sample surface over the two-dimensional area to be observed.

2. A high resolution observation apparatus according to claim 1; wherein the optical device is an optical prism made of a transparent material and having a flat surface on which the sample material to be observed is coated.

3. A high resolution observation apparatus according to claim 1; wherein the optical detecting probe comprises a optical fiber having a sharpened tip portion for detecting the sample light, a light shielding film on an end surface of the optical fiber for optically shielding all of the end surface except the opening at a very end portion of the tip portion, a core portion for guiding the sample light received by the tip portion, and a clad portion which covers the core portion coaxially.

4. A high resolution observation apparatus according to claim 3; wherein the opening at the tip portion of the optical detecting probe is smaller in size than a wavelength of the incident light.

5. A high resolution observation apparatus according to claim 1; wherein the optical detecting probe comprises a light guide formed on a semiconductor thin film in a shape of a cantilever.

6. A high resolution observation apparatus according to claim 1; wherein the optical source generates the incident light by one of a mercury lamp, xenon lamp, and halogen lamp.

7. A high resolution observation apparatus according to claim 1; wherein the optical source generates an incident light by one of a helium-neon laser, argon ion laser, and semiconductor laser.

8. A high resolution observation apparatus according to claim 1; wherein the optical source further generates an incident light having at least two wavelengths.

9. A high resolution observation apparatus according to claim 1; wherein the optical detecting system detects an evanescent light emitted from the sample surface in response to the incident light.

10. A high resolution observation apparatus according to claim 1; wherein the optical detecting system detects the sample light having a wavelength which is the same as the predetermined wavelength of the incident light.

11. A high resolution observation apparatus according to claim 1; wherein the optical detecting system discriminates and detects a fluorescent condition of the sample.

12. A high resolution observation apparatus according to claim 1; wherein the z-axis control unit includes means for fixing a position of the optical detecting probe at a distance above the sample surface close enough to detect the sample light during a course of scanning the sample surface over the two-dimentional area to be observed.

13. A high resolution observation apparatus according to claim 1; wherein the z-axis control unit includes means for controlling a position of the optical detecting probe so as to keep a positioning signal detected as a tunnel current flowing between a part of the optical probe and the sample surface constant during a course of scanning the sample surface over the two-dimentional area to be observed.

14. A high resolution observation apparatus according to claim 1; wherein the z-axis control unit includes means for controlling a position of the optical detecting probe so as to keep a positioning signal detected as an interatomic force between a part of the optical probe and the sample surface constant during a course of scanning the sample surface over the two-dimentional area to be observed.

15. A high resolution observation apparatus according to claim 1; wherein the z-axis control unit includes means for controlling a position of the optical detecting probe so as to keep a positioning signal detected as a physical parameter between a part of the optical probe and the sample surface constant during a course of scanning the sample surface over the two-dimentional area to be observed.

16. A high resolution observation apparatus according to claim 1; wherein the optical source generates an incident light having at least two wavelengths, and the optical detecting system discriminates each wavelength of the sample light from the sample caused by the incident light and detects an intensity of each wavelength of the sample light, one detected signal corresponding to one wavelength of the sample light being utilized for controlling the z-axis position of the optical detecting probe by the z-axis control unit so as to keep the detected signal constant, and another detected signal corresponding to another wavelength of the sample light being utilized for observing optical constants of the sample material during a course of scanning the sample surface over the two-dimentional area to be observed.

17. A high resolution observation apparatus according to claim 1; wherein the optical source generates an incident light having a wavelength which affects a spot area of the sample material by irradiation of the incident light, and the optical detecting system detects the spot area affected to a different state from a rest of the sample material.

* * * * *